(12) United States Patent
Ortiz et al.

(10) Patent No.: US 7,393,688 B2
(45) Date of Patent: Jul. 1, 2008

(54) METHOD OF USING A HEMATOLOGY REFERENCE CONTROL FOR MEASUREMENT OF IMMATURE GRANULOCYTES

(75) Inventors: Nery Ortiz, Miami, FL (US); Theodore J. Gerula, Fort Lauderdale, FL (US); Yi Li, Miami, FL (US)

(73) Assignee: Beckman Coulter, Inc., Fullerton, CA (US)

( * ) Notice: Subject to any disclaimer, the term of this patent is extended or adjusted under 35 U.S.C. 154(b) by 52 days.

(21) Appl. No.: 11/495,056

(22) Filed: Jul. 28, 2006

(65) Prior Publication Data

US 2007/0020611 A1 Jan. 25, 2007

Related U.S. Application Data

(62) Division of application No. 10/845,557, filed on May 13, 2004, now Pat. No. 7,109,036.

(51) Int. Cl.
*G01N 31/00* (2006.01)

(52) U.S. Cl. .................. 436/8; 436/10; 436/16; 436/967

(58) Field of Classification Search ............. 436/8, 436/10, 16
See application file for complete search history.

(56) References Cited

U.S. PATENT DOCUMENTS

| | | | |
|---|---|---|---|
| 3,873,467 A | 3/1975 | Hunt | |
| 4,213,876 A | 7/1980 | Crews et al. | |
| 4,264,470 A | 4/1981 | Chastain et al. | |
| 4,299,726 A | 11/1981 | Crews et al. | |
| 4,358,394 A | 11/1982 | Crews et al. | |
| 4,389,490 A | 6/1983 | Crews et al. | |
| 4,405,719 A | 9/1983 | Crews et al. | |
| 4,704,364 A | 11/1987 | Carver et al. | |
| 5,084,394 A | 1/1992 | Vogt et al. | |
| 5,308,772 A * | 5/1994 | Sakata et al. | 436/63 |
| 5,320,964 A | 6/1994 | Young et al. | |
| 5,380,664 A | 1/1995 | Carver et al. | |
| 5,512,485 A | 4/1996 | Young et al. | |
| 5,837,547 A | 11/1998 | Schwartz | |
| 5,958,776 A | 9/1999 | Sakata et al. | |
| 6,200,500 B1 | 3/2001 | Ryan | |
| 6,221,668 B1 | 4/2001 | Ryan et al. | |
| 6,399,388 B1 | 6/2002 | Ryan et al. | |
| 6,403,377 B1 | 6/2002 | Ryan et al. | |
| 6,406,915 B2 | 6/2002 | Ryan et al. | |
| 6,569,682 B2 | 5/2003 | Elliott et al. | |
| 6,916,658 B2 | 7/2005 | Li et al. | |
| 7,109,036 B2 * | 9/2006 | Ortiz et al. | 436/8 |
| 2004/0171164 A1 * | 9/2004 | Li et al. | 436/63 |

* cited by examiner

*Primary Examiner*—Ralph Gitomer
(74) *Attorney, Agent, or Firm*—Cuspa Technology Law Associates; Mitchell E. Alter

(57) ABSTRACT

A method of using a reference control for measurement of immature granulocytes on a blood analyzer is disclosed. The method includes analyzing a reference control that contains an immature granulocyte component made of processed red blood cells for simulating immature granulocytes and a mature white blood cell component for simulating white blood cells of a blood sample on a blood analyzer adapted for measurement of immature granulocytes, and reporting the immature granulocyte component and the mature white blood cell component of the reference control.

13 Claims, 4 Drawing Sheets

METHOD OF USING A HEMATOLOGY REFERENCE CONTROL FOR MEASUREMENT OF IMMATURE GRANULOCYTES

CROSS-REFERENCE TO RELATED APPLICATION

The present application is a Divisional of patent application Ser. No. 10/845,557 filed on May 13, 2004, which is now U.S. Pat. No. 7,109,036 B2, the contents of which are incorporated in this disclosure by reference in their entirety.

FIELD OF THE INVENTION

The present invention relates to a hematology reference control composition containing an immature granulocyte component and the method of making and using the hematology reference control composition for determination of immature granulocytes of a blood sample on a blood analyzer.

BACKGROUND OF THE INVENTION

The presence of immature granulocytes (IG) in peripheral blood is potentially important information which indicates enhanced bone marrow activation. Besides the obvious significance of blasts for the diagnosis of leukaemia, the promyelocyte, myelocyte and metamyelocyte stages of myeloid maturation may indicate systemic inflammatory stress or leukaemic reactions. The determination of immature granulocytes is routinely done by visual microscopy, which requires manual review of each blood sample smear, and is a labor intensive and time consuming task.

Currently, several high end hematology analyzers which utilize optical, fluorescence and impedance measurements to provide automated determination of immature granulocytes of the blood samples. U.S. Pat. No. 5,958,776 (to Sysmex) teaches a lytic reagent and a method of measuring immature granulocytes using light scatter and fluorescence measurements. However, these instruments and their detection systems are expensive, and not suitable for low cost analyzers. Therefore, there is a need for automated and inexpensive determination of immature granulocytes and reduction of manual review rate.

On the other hand, quality control has long been a necessary and routine procedure in clinical hematology. Accuracy in the counting of various types of blood cells is dependent, in part, upon the use of adequate control products and methods of using the control products. With the numerous types of equipment for particle counting now available, quality control by the use of control products is necessary, since the possibility of an instrument malfunctioning is ever present. The traditional method of maintaining a quality control program for automatic particle counting equipment has consisted of providing fresh human blood as a whole blood standard. However, this fresh blood is usable for only one day, therefore, various manufactured control products which have longer product lifetime have been developed.

Commonly used particles in a control product simulate or approximate the types of particles or cells that are intended to undergo analysis. Consequently, these particles have been frequently referred to as analog particles. The analog particles should be selected or designed so that they have certain characteristics that are similar to those of the particles or cells to be analyzed in the instruments. Exemplary characteristics and parameters include similarities in size, volume, surface characteristics, granularity properties, light scattering properties and fluorescence properties.

Various commercial reference control products are now available, which use various processed or fixed human or animal blood cells as analogs of human blood cells. U.S. Pat. No. 4,704,364 (to Carver et al) teaches a hematology control comprising three white blood cell analogs made of fixed animal red blood cells for differential analysis of white blood cells into three subpopulations using DC impedance measurement. U.S. Pat. No. 5,512,485 (to Young et al) teaches a hematology control comprising several white blood cell analogs made of processed and fixed animal red blood cells for differential analysis of white blood cells into five subpopulations using light scatter, radio frequency and DC impedance measurements, commonly referred to as the VCS method.

However, currently no hematology reference control provides an immature granulocyte component, which enables quality control of the immature granulocyte measurement.

Based on the foregoing, there exists a need for a hematology reference control which comprises an immature granulocyte component for quality control of the immature granulocyte measurement.

SUMMARY OF THE INVENTION

In one embodiment, the present invention provides a hematology reference control containing an immature granulocyte component, which comprises an immature granulocyte component made of processed non-human blood cells for simulating human immature granulocytes and a suspension medium suitable for delivering the component to a blood analyzer for measurement of immature granulocytes. The immature granulocyte component is in a size range from about 2% to about 85% larger than a high end of the size range of human granulocytes when measured by a blood analyzer. The immature granulocyte component can be made of processed avian, reptile, or fish red blood cells, such as emu, ostrich, alligator, or shark red blood cells.

The hematology reference control can further include a nucleated red blood cell component. Moreover, the hematology reference control can also include a mature white blood cell component which can comprise white blood cell subcomponents for simulating white blood cell subpopulations. Additionally, the hematology reference control can further include a red blood cell component, a platelet component, and a reticulocyte component.

In a further embodiment, the present invention provides a hematology reference control containing an immature granulocyte component, which comprises a mature white blood cell component simulating human mature white blood cells on a blood analyzer; an immature granulocyte component for simulating human immature granulocytes; and a suspension medium suitable for delivering the components to the blood analyzer for measurement of immature granulocytes. In addition to the processed avian, reptile, or fish red blood cells, processed human immature granulocytes can also be used as the immature granulocyte component in the reference control. The human immature granulocytes can be grown in vitro by a cell line.

In another embodiment, the present invention provides a hematology reference control containing an immature granulocyte component, which comprises a first processed red blood cell from a first species as a lymphoid component; a second processed red blood cell from a second species as a myeloid component; a third processed red blood cell from a third species as an immature granulocyte component; and a suspension medium suitable for delivering the components to a blood analyzer for measurement of immature granulocytes.

In a yet further embodiment, the present invention is directed to a method of using the hematology reference control containing an immature granulocyte component. The method includes the steps of providing a reference control containing an immature granulocyte component; providing a blood analyzer adapted for analyzing immature granulocytes; passing the reference control through the blood analyzer for detection of the immature granulocyte component; and reporting the immature granulocyte component in the reference control. The measurement of immature granulocytes can be performed using impedance measurement, and optical measurement including light scatter measurement and axial light loss measurement.

DETAILED DESCRIPTION OF THE INVENTION

Figure 1:
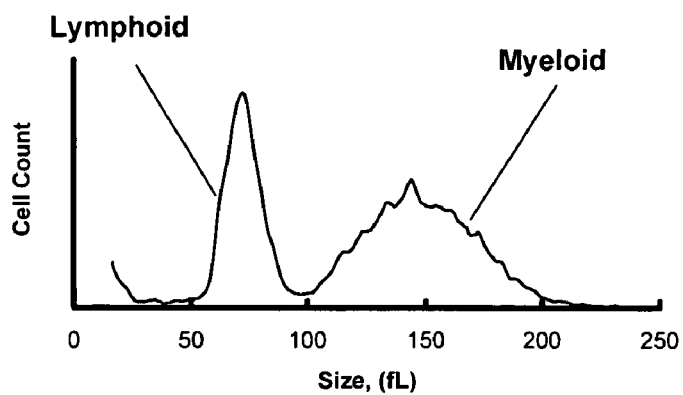
FIG. 1 shows a DC histogram of a normal whole blood sample analyzed according to the procedure described in Example 4.

In one embodiment, the present invention provides a hematology reference control composition that contains an immature granulocyte component. More specifically, the reference control composition comprises an immature granulocyte component made of processed non-human blood cells for simulating human immature granulocytes, and a suspension medium suitable for delivering the component to a blood analyzer for measurement of immature granulocytes. The immature granulocytes referred herein include myelocytes, promyelocytes, metamyelocytes, myeloblasts and promyeloblasts. For the purpose of the present invention, the immature granulocyte component, as well as other cell type components, are also referred to as analogs, for example, immature granulocyte (IG) analog.

Suitable examples of non-human blood cells suitable for simulating human immature granulocytes include various animal red blood cells including, but not limited to, avian, reptile and fish red blood cells. More specifically, emu, ostrich, alligator, and shark red blood cells can be used. In general, immature granulocytes are larger in size than mature white blood cells, more particularly, their average cell volume is larger than that of granulocytes. The analog should simulate the properties of human immature granulocytes under a sample preparation condition and by the measurement method used for the white blood cell analysis. In general, the immature granulocyte analog can be made in a size range from about 2-85% larger than the high end of the size range of human granulocytes when measured by a blood analyzer.

In a further embodiment, the immature granulocyte component can be made of fixed human immature granulocytes which are grown in vitro by a immature granulocyte cell line.

In one embodiment, emu red blood cells were used for making the immature granulocyte analog. To prepare the immature granulocyte analog, the emu red blood cells in a quality of emu whole blood is separated first from other blood components including white blood cells, platelets and plasma by centrifugation. The emu red blood cells are washed by an isotonic wash solution. The washed emu red blood cells are then processed by a processing medium, by incubating the cells in the processing medium with slow mixing for a period of time, preferably from about 8 to about 28 hours. The processed emu red blood cells are washed again and suspended in a suspension medium for storage and use on a blood analyzer.

One suitable wash solution is the phosphate buffered saline solution (PBS). Other wash solution known to those skilled in the art can also be used. The processing medium comprises a fixative and an osmolarity adjustment agent for providing appropriate osmolarity of the processing medium, depending on the source of the blood cells and required property of the analog. Suitable examples of the osmolarity adjustment agents include, but are not limited to, alkaline metal phosphate, alkaline metal chloride and alkaline metal sulfate. Suitable examples of the fixative include, but are not limited to, formaldehyde, glutaraldehyde and paraformaldehyde. The concentration of the fixative is in a range from about 0.5% to about 1.5%.

One suitable example of the suspension medium includes phosphate buffered saline solution and an aqueous solution of a plasma substance. As defined herein, an aqueous solution of a plasma substance comprises an aqueous solution of a serum substance, serum substance in combination with a plasma protein and mixtures thereof. As further defined herein, plasma protein comprises one or more of the proteins contained in plasma. Preferably, such plasma proteins comprise albumin, lipoproteins, globulins, fibrinogens and mixtures thereof. These media may contain other ingredients known to those skilled in the art to confer long term stability. Other examples of suitable medium are more fully described in U.S. Pat. Nos. 4,213,876, 4,299,726, 4,358,394, 3,873,467, 4,704,364, 5,320,964, 5,512,485 and 6,569,682 which are herein incorporated by reference in their entirety.

Example 1 illustrates an exemplary process of preparing an immature granulocyte analog using emu red blood cells. Example 2 illustrates an exemplary process of preparing an immature granulocyte analog using alligator red blood cells. The immature granulocyte analogs made of emu red blood cells and alligator red blood cells have different sizes, which can be used for the measurement methods having different detection dynamic ranges.

In an alternative embodiment, the immature granulocyte analog can also be made of more than one type of processed blood cells. Immature granulocytes in the clinical samples have a broad size distribution, and they can extend from the high end of granulocytes to a size about twice that of the granulocytes. To simulate such a broad size distribution, a mixture of two different processed blood cells which have an overlap in size distribution can be used.

In a further embodiment, the hematology reference control composition can further comprise a mature white blood cell component for measurement of white blood cells (WBC) and immature granulocytes. Moreover, the mature white blood cell component can further comprise sub-components for simulating subpopulations of white blood cells, such as lymphoid cells, myeloid cells (the sum of monocytes and granulocytes), or further into lymphocytes, monocytes, neutrophils, eosinophils and basophils, which can be utilized as a reference control for differential analysis of white blood cells.

Suitable examples of white blood cell analogs include stabilized and fixed mammalian white blood cells, and processed and/or fixed human and animal red blood cells, as known in the art. In one embodiment, the white blood cell analogs can be made from processed avian and human red blood cells for differential analysis using an impedance measurement, as taught in U.S. Pat. No. 4,704,364, which is herein incorporated by reference in its entirety. In a further embodiment, the white blood cell analogs can be made from fixed mammalian white blood cells. The mammalian white blood cells are fixed prior to lysing the red blood cells in the whole blood during the preparation of the white blood cell analogs. In another embodiment, the white blood cell analogs can be made from processed goose and alligator red blood cells for differential analysis using a combination of impedance and light scatter measurement, as taught in U.S. Pat. Nos. 5,320,964 and 5,512,485, which are herein incorporated by reference in their entirety.

Optionally, the mammalian white blood cells and the human and animal red blood cells can be further processed by contacting with a lipoprotein during the process of preparing the white blood cell analogs. The contact with lipoprotein can occur prior to fixing the white or red blood cells, it can also occur after fixing and during storage in the suspension medium, as taught in U.S. Pat. Nos. 5,320,964, 5,512,485, 6,406,915, 6,403,377, 6,399,388, 6,221,668, and 6,200,500 which are incorporated herein by reference in their entirety.

Example 3 illustrates an exemplary process of preparing reference control compositions which contained white blood cell sub-components and an immature granulocyte component. Three reference control compositions, A, B and C were prepared. The reference control composition A contained 30% lymphoid analog made of processed human red blood cells and 70% myeloid analog made of processed goose red blood cells. The processes of making lymphoid and myeloid analogs are described in detail in Example 3. The reference control composition B contained 30% lymphoid analog made of processed human red blood cells, 49% myeloid analog made of processed goose red blood cells, and 21% immature granulocyte analog made of processed emu red blood cells of Example 1. The reference control composition C contained 25% lymphoid analog made of processed human red blood cells, 58% myeloid analog made of processed emu red blood cells of Example 1, and 17% immature granulocyte analog made of processed alligator red blood cells of Example 2.

It is noted that the analog made of processed emu red blood cells was used for two different purposes, one as an immature granulocyte analog in reference control composition B, and the other as a myeloid analog in reference control composition C. Reference control compositions B and C have different cell size ranges, and can be used for the measurement having different dynamic ranges. The former can be used for the measurement using a smaller dynamic range, which has a higher resolution for the blood cells measured, more suitable for a concurrent measurement of measurement of immature granulocytes and nucleated red blood cells. The latter can be used for the measurement having a larger dynamic range, which allows the measurement of extremely large immature granulocytes.

These reference control compositions were utilized for measurement of white blood cells and immature granulocytes using a DC impedance measurement as shown in Example 4. The measurement method and instrumentation used for the measurement were described in co-pending patent application Ser. No. 10/770,193, filed on Feb. 2, 2004, (now U.S. Pat. No. 6,916,658 issued on Jul. 17, 2005) entitled "Method for Measurement of Immature Granulocytes", which is herein incorporated by reference in its entirety. Moreover, the instrumentation and the reagents used are described in detail in Example 4.

Figure 2:
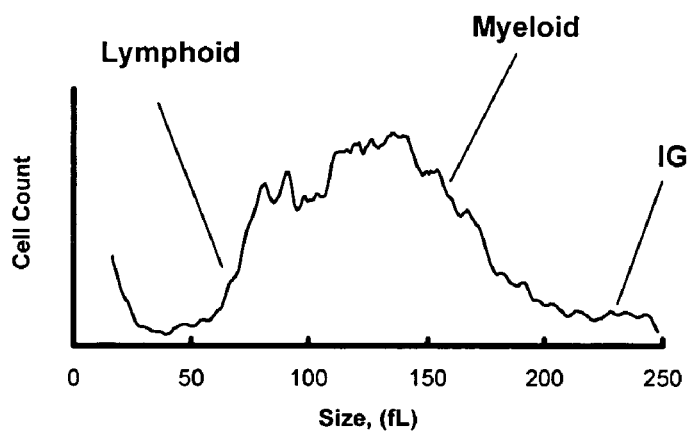
FIGS. 2 and 2A show DC histograms of two clinical samples containing immature granulocytes analyzed according to the procedure described in Example 4.
Figure 2A:
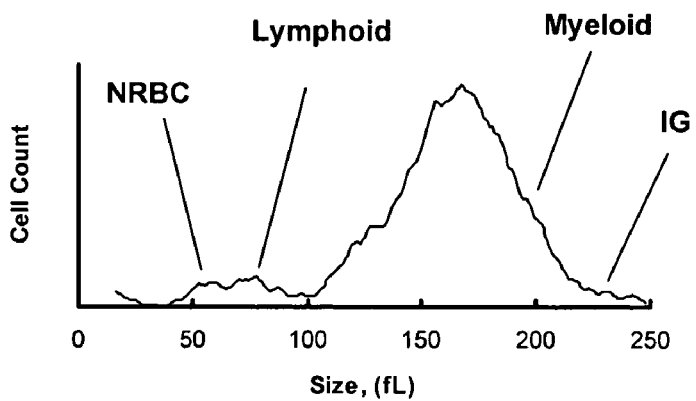

FIG. 1 shows a DC histogram of a normal whole blood sample analyzed on the experimental hematology analyzer. For a normal blood sample, the white blood cells had a bi-modal distribution, with the lymphoid subpopulation on the left and the myeloid subpopulation on the right. No cell population located on the right side of the myeloid subpopulations. FIG. 2 shows the DC histogram of a clinical sample containing about 12% of immature granulocytes (IG), including metamyelocytes, myelocytes and promyelocytes. As shown, immature granulocytes showed on the right side of the myeloid subpopulation. FIG. 2A shows the DC histogram of another clinical sample containing about 6% of immature granulocytes including metamyelocytes and myelocytes, which were indicated by the large cells extending into the right-most region of the histogram. This sample also contained 5 NRBC per 100 WBC, which located on the left side of the lymphoid population.

Figure 3:
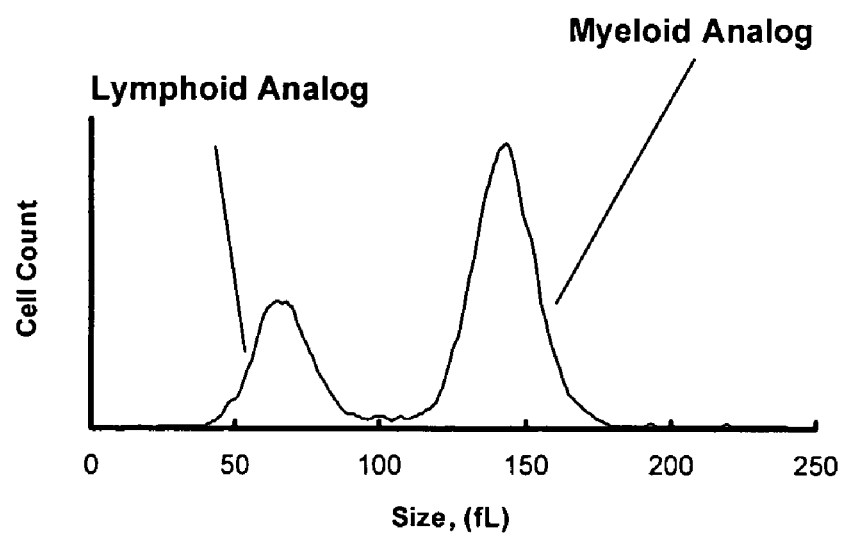
FIG. 3 shows a DC histogram of the reference control composition A of Example 3, which contained only white blood cell sub-components.
Figure 4:
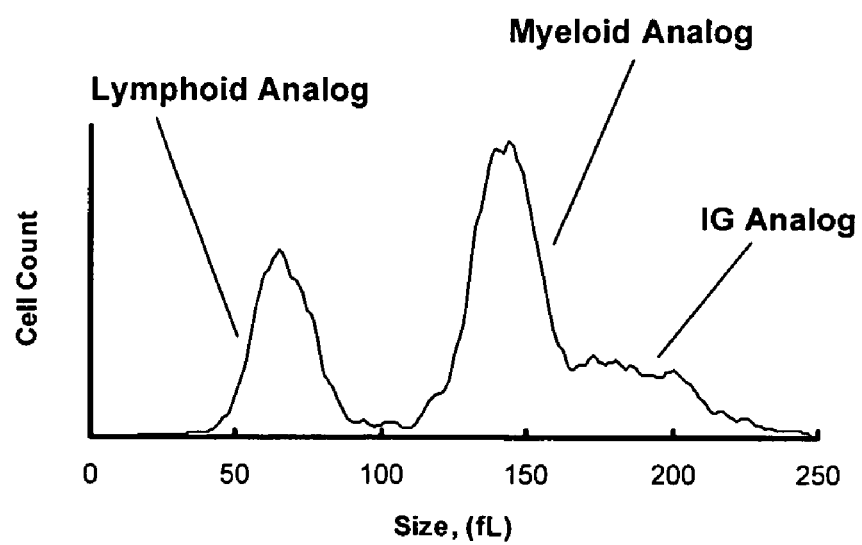
FIG. 4 shows a DC histogram of the reference control composition B of Example 3, which contained white blood cell sub-components and an immature granulocyte component made of emu red blood cells.

FIGS. 3 and 4 show DC histograms of reference control compositions A and B analyzed on the same instrument. As shown, the histogram of the reference control composition A resembles the cell distribution of the normal blood sample, and the histogram of the reference control composition B resembles the cell distribution of the clinical sample containing immature granulocytes. Using the reference control, one can determine the presence of immature granulocytes, hence, providing a quality assurance for the instrument and the detection method.

Figure 5:
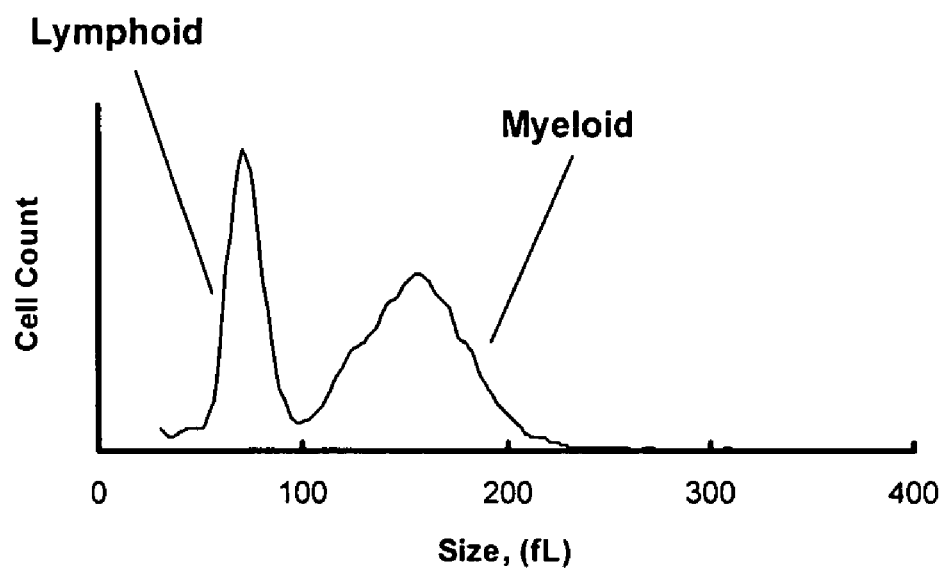
FIG. 5 shows a DC histogram of a normal whole blood sample analyzed according to the procedure described in Example 4, and measured with a larger dynamic range.
Figure 6:
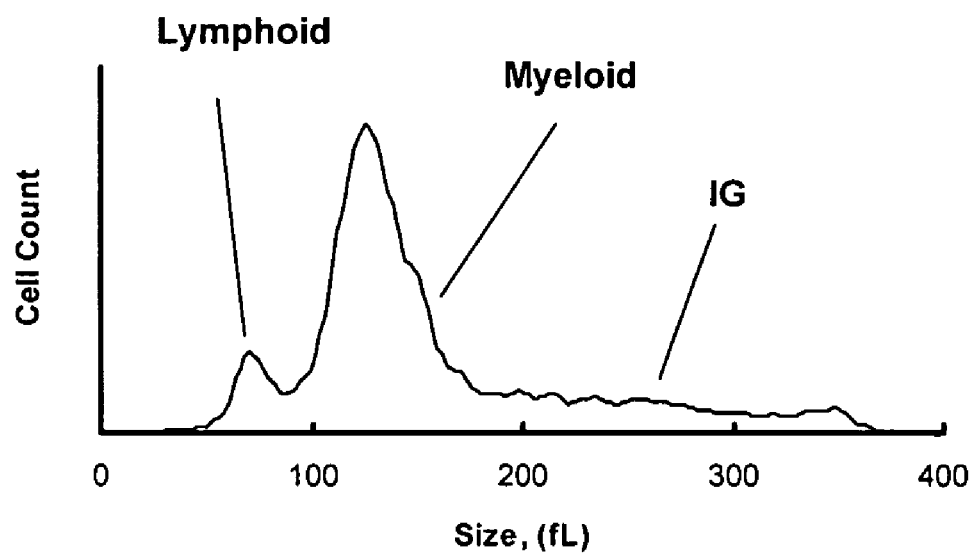
FIG. 6 shows a DC histogram of a clinical blood sample analyzed according to the procedure described in Example 4, and measured with the same dynamic range used in FIG. 5.

FIGS. 5 and 6 show DC histograms of a normal whole blood sample and a clinical sample containing immature granulocytes analyzed on the experimental hematology analyzer, but with a larger dynamic range of the measurement. With the larger dynamic range, normal white blood cells distributed in approximately only half of the histogram. The manual reference reported the clinical sample having about 24% of immature granulocytes (IG), including metamyelocytes, myelocytes and promyelocytes. As shown, some of the immature granulocytes were very large and had a cell size close to double of the granulocytes which constitute the majority of the myeloid population.

Figure 7:
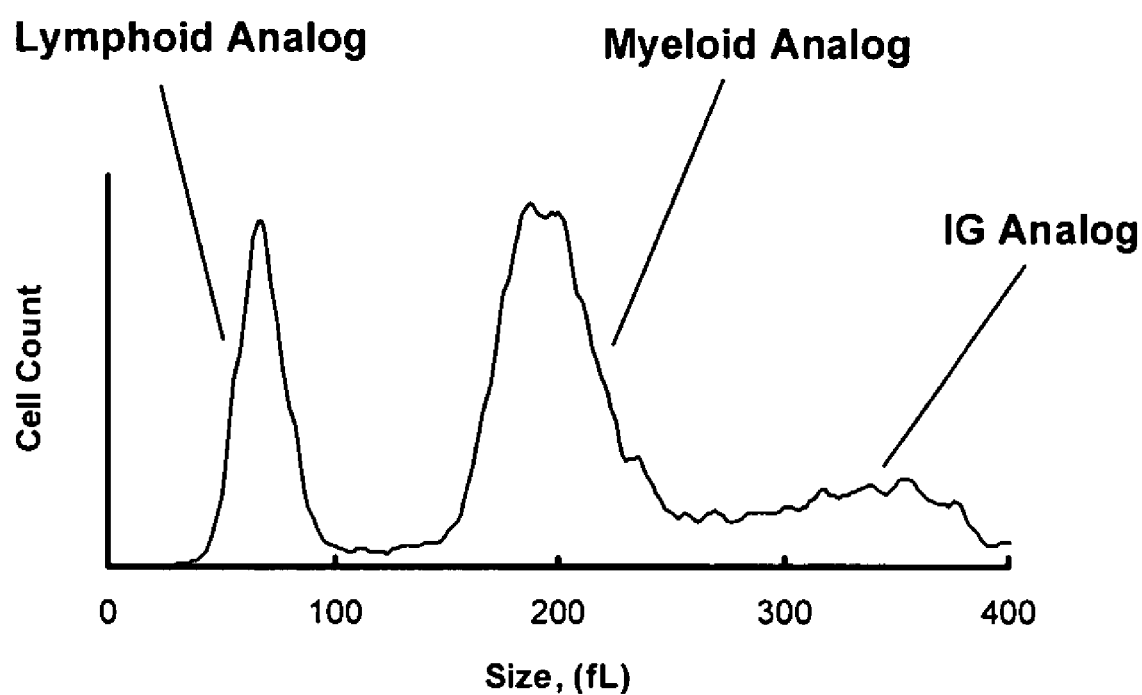
FIG. 7 shows a DC histogram of the reference control composition C of Example 3, which contained white blood cell sub-components and an immature granulocyte component made of alligator red blood cells, measured with the same dynamic range used in FIG. 5.

FIG. 7 shows the DC histogram of the reference control composition C analyzed on the experimental hematology analyzer with the same dynamic range shown in FIG. 5. As shown, the histogram of the reference control composition C resembles the cell distribution of the clinical sample containing immature granulocytes measured under the same condition.

It should be understood that although the reference control containing an immature granulocyte component as described above is analyzed by a DC impedance measurement, it can also be used for radio frequency (RF) impedance measurement, and optical measurement. It is known that the forward light scatter or low angle light scatter measurement reflects the size of cells. Furthermore, axial light loss measurement, which measures the light loss due to absorption and scattering of a cell passing through a light beam, also reflects the size of cells. Therefore, the immature granulocyte analog prepared using the method of the present invention can also be used with these measurement methods.

In another embodiment, the reference control containing an immature granulocyte component and sub-components of white blood cells, as described previously, can also be used for differential analysis of white blood cells into two, three or five subpopulations.

In a yet further embodiment, the reference control composition can further comprise a nucleated red blood cell component for simulating nucleated red blood cells of a blood sample on a blood analyzer. Nucleated red blood cells are immature red blood cells present in clinical samples due to certain clinical conditions, which are usually detected together with white blood cells, since both are nucleated cells. The nucleated red blood cells are reported either as the numbers of NRBC per 100 WBC, or absolute concentration. The methods of making a nucleated red blood cell analog have been described in the co-pending patent applications Ser. No. 10/689,245 (now abandoned) and 60/560,236 (now converted into U.S. Non provisional patent application Ser. No. 11/094,644 filed on Mar. 30, 2005), which are incorporated herein by reference in their entirety.

Example 5 illustrates a preparation of a reference control composition containing an immature granulocyte component, a white blood cell component that includes two sub-components as described above, and a nucleated red blood cell component. This reference control can be used for measurement of white blood cells, immature granulocytes and nucleated red blood cells using a DC impedance measurement.

Depending on the reaction condition and detection method, the reference control composition containing both an immature granulocyte component and a nucleated red blood cell component can be either used for a simultaneous measurement of both immature granulocytes and nucleated red blood cells, or for two separate measurements, one for each cell population. The latter is commonly utilized on automated hematology analyzers, which aspirate a blood sample and segment it into several aliquots for separate sample preparations and analyses by the analyzer.

In another embodiment, the reference control composition further comprises a red blood cell component and a platelet component in the suspension medium. The red blood cell component can be stabilized human or animal red blood cells, preferably, stabilized human red blood cells. The process of making red blood cell component has been described in details in U.S. Pat. Nos. 4,299,726 and 4,358,394. The platelet component can be stabilized human or animal platelets, or platelet analogs made from other cell types. One suitable example is processed goat red blood cells as the platelet analog, as disclosed in U.S. Pat. Nos. 4,264,470, 4,389,490 and 4,405,719, which are incorporated by references in their entirety.

The red blood cells of a blood sample or the stabilized human red blood cells in the reference control composition are lysed under lysing conditions normally used for preparing a blood sample for the measurement of white blood cells, and should not be detected in the measurement if the analyzer operates properly. The platelets of a blood sample under the lysing conditions are reduced in size and they are either below the detection threshold for the measurement of white blood cells or nucleated red blood cells, or are separated from the nucleated blood cells. The platelet analog described above simulates the response of the platelets of a blood sample under the lysing condition. Therefore, the red blood cell component and platelet component in the reference control composition further reflect the response of the control composition to the lysing reagent, as well as the reaction conditions on the instrument. Hence, the hematology reference control composition containing red blood cell and platelet components can provide further information related to instrument operating conditions.

Furthermore, the reference control composition can further comprise a reticulocyte component for simulating reticulocytes of a blood sample on a blood analyzer. Moreover, the hematology reference control composition containing red blood cell component, platelet component and reticulocyte component can also be used for the red blood cell and platelet measurements, which are commonly performed together with the measurement of the white blood cells on an automated hematology analyzer.

Example 6 illustrates an exemplary process of preparing a reference control composition containing an immature granulocyte component, a white blood cell component that includes two sub-components, i.e., a lymphoid component and a myeloid component, a red blood cell component and a platelet component.

The following examples are illustrative of the invention and are in no way to be interpreted as limiting the scope of the invention, as defined in the claims. It will be understood that various other ingredients and proportions may be employed, in accordance with the proceeding disclosure.

EXAMPLE 1

Immature Granulocyte Component Made of Emu Red Blood Cells

| Phosphate Buffered Saline Solution (PBS) | |
| --- | --- |
| Sodium dihydrogenphosphate: | 0.2 g |
| Disodium hydrogenphosphate 7H$_2$O: | 2.0 g |
| Sodium azide: | 0.1 g |
| Sodium chloride: | 9.4 g |
| Qs to 1 liter with distilled water: | pH approximately 7.4 osmolarity 315 to 345 mOsm/kg H$_2$O |

| Analog Processing Medium 1 | |
| --- | --- |
| Disodium hydrogenphosphate 7H$_2$O: | 2.0 g |
| Sodium dihydrogenphosphate: | 0.2 g |
| Sodium chloride | 24.5 g |
| Glutaraldehyde (25%) | 40 ml |
| Qs to 1 liter with distilled water: | pH approximately 7.4 osmolarity 900 mOsm/kg H$_2$O |

| Suspension Medium 1 | | |
| --- | --- | --- |
| Component | Range (g/liter) | Preferred (g/liter) |
| Xanthine compound | 1-10 | 2-7 |
| Adenosine monophosphate | 0.1-1.0 | 0.2-0.8 |
| Inosine | 0.1-1.0 | 0.2-0.8 |
| pH adjusting agents sufficient to obtain | pH 5.8-6.8 | pH 6.0-6.5 |
| Osmolarity adjusters sufficient to obtain | 200-400 mOsm | 250-350 |
| Preservative | effective amount | 2.0-6.0 |
| Qs to 1 liter with distilled water | | |

| Suspension Medium 2 | |
| --- | --- |
|  | Preferred (g or ml/liter) |
| Propyl paraben | 0.3 to 1.0 g |
| Methyl paraben | 0.5 to 1.0 g |
| Procaine hydrochloride | 0.1 to 0.5 g |
| Deoxycholic acid | 0.1 to 0.9 g |
| Lactose | 10.0 to 50.0 g |
| Actidione | 0.1 to 0.6 g |
| Trisodium citrate dehydrate | 3.0 to 8.0 g |
| Citric acid monohydrate | 0.3 to 0.9 g |
| Sodium dihydrogenphosphate monohydrate | 0.8 to 2.5 mg |
| Phenergan hydrochloride | 0.1 to 1.0 g |
| Colistimethate, sodium | 0.2 to 0.9 g |
| Penicillin G., sodium | $0.5 \times 10^6$ to $3 \times 10^6$ units |
| Kanamycin sulfate | 0.2 to 0.8 g |
| Neomycin sulfate | 0.2 to 1.0 g |
| 5'-AMP | 0.4 to 1.0 g |
| Adenine | 0.2 to 0.8 g |
| Inosine | 0.4 to 1.0 g |
| Dihydrostreptomycin sulfate | 0.2 to 1.0 g |
| Tetracycline hydrochloride | 0.2 to 1.0 g |
| 30% Bovine albumin | 100 to 350 ml |
| Qs to 1 liter with distilled water | |

Process steps for preparing immature granulocyte analog using emu red blood cells:

1. 50 ml of emu whole blood was collected in an anticoagulant containing container. The emu whole blood was centrifuged and the top layer (including white blood cells, platelets and plasma) was removed.

2. The packed emu red blood cells was washed three times with the phosphate buffered saline solution (PBS), and the washed packed cells was re-suspend in the residual PBS. The cell washing steps were a series of centrifugations (1000 rpm/5 minutes), followed by removal of the supernatant and re-suspension of the packed cells with PBS.

3. 1 ml of packed emu red blood cells was added into a test tube containing 49 ml of the Analog Processing Medium 1, and mixed by inversion to form a cell processing suspension.

4. The test tube was placed on a roller and mixed at a slow speed overnight at room temperature.

5. The processed cells were then washed three times with PBS, as described in step (1).

6. The processed cells was re-suspended in the Suspension Medium 1 or 2 to form an immature granulocyte reference control for analysis on a blood analyzer.

EXAMPLE 2

Immature Granulocyte Component Made of Alligator Red Blood Cells

An amount of alligator whole blood was collected and processed with the same process steps described in Example 1, except that in step 3 the Analog Processing Medium 2 shown below was used. The processed alligator red blood cells were resuspended in Suspension Medium 1 to form another immature granulocyte reference control.

| Analog Processing Medium 2 | |
| --- | --- |
| Sodium chloride | 31.7 g |
| Glutaraldehyde (25%) | 40 ml |
| Qs to 1 liter with distilled water: | pH approximately 6.5 osmolarity 1000 mOsm/kg $H_2O$ |

As shown in Example 3 hereinafter, the immature granulocyte analog made of alligator red blood cells are larger in size than that made of emu red blood cells, and can be used to simulate human immature granulocytes in a larger dynamic range of the measurement.

EXAMPLE 3

Hematology Reference Control Composition Containing an Immature Granulocyte Component and White Blood Cell Sub-Components 1. Lymphoid Analog The lymphoid analog was made of fixed human red blood cells. The process has been described in detail in U.S. Pat. No. 4,704,364, which is herein incorporated by reference in its entirety.

2. Myeloid Analog

The myeloid analog was prepared by processing goose red blood cells using the process described in Example 1, except that in step 3 the Analog Processing Medium 3 shown below was used.

| Analog Processing Medium 3 | |
| --- | --- |
| Disodium hydrogenphosphate $7H_2O$: | 2.0 g |
| Sodium dihydrogenphosphate: | 0.2 g |
| Sodium chloride | 16.5 g |
| Glutaraldehyde (25%) | 40 ml |
| Qs to 1 liter with distilled water: | pH approximately 7.4 osmolarity 550 mOsm/kg $H_2O$ |

3. Prepare the Reference Control Composition

Procedure:

1. Provide a predetermined volume of the Suspension Medium 1 described in Example 1.

2. Add predetermined amounts of lymphoid and myeloid analogs in the suspension medium.

3. Add a predetermined amount of immature granulocyte analog in the suspension medium.

The proportion of the three analogs resembles the white blood subpopulations and immature granulocytes in normal and abnormal human whole blood. As a reference control resembling a normal human blood, the control composition does not contain immature granulocyte analog. As a reference control resembling a clinical sample containing immature granulocytes, the control composition can contain a certain amount of immature granulocyte analog, for example, about 10% to 50% of the total white blood cells.

Following reference control compositions were made using the process described above:

(1) Reference Control Composition A, Containing:

30% lymphoid analog made of processed human red blood cells of Example 3; and

70% myeloid analog made of processed goose red blood cells of Example 3.

(2) Reference Control Composition B, Containing:
   30% lymphoid analog made of processed human red blood cells of Example 3;
   49% myeloid analog made of processed goose red blood cells of Example 3; and
   21% immature granulocyte analog made of processed emu red blood cells of Example 1.

(3) Reference Control Composition C, Containing:
   25% lymphoid analog made of processed human red blood cells of Example 3;
   58% myeloid analog made of processed emu red blood cells of Example 1; and
   17% immature granulocyte analog made of processed alligator red blood cells of Example 2.

Reference control compositions B and C have different size ranges, and can be used for the measurements having different dynamic ranges, as described hereinafter in Example 4. As shown in the compositions, the analog made of processed emu red blood cells can be used as an immature granulocyte analog, as in reference control composition B, and can also be used as a myeloid analog, as in reference control composition C.

EXAMPLE 4

Use of the Hematology Reference Control on a Hematology Analyzer for Measurement of Immature Granulocytes Using a DC Impedance Measurement The reference control compositions described in Example 3 were analyzed on an experimental hematology analyzer. In the analysis, an aliquot of 28 μl of the reference control or a blood sample was diluted with 6 ml of Coulter® LH Series Diluent (Beckman Coulter, Inc., Miami, Fla.) in a WBC bath, then mixed with 1 ml of a lytic reagent composition to lyse red blood cells. The lytic reagent contained 25.0 g/L of tetradecyltrimethylammonium bromide, 15.0 g/L of Igepal SS-837 (an ethoxylated phenol from RhÔne-Poulenc), 4.0 g/L of Plurofac A38 prill surfactant (from BASF Corp.), and had a pH of 6.2. The experimental hematology analyzer was a modified LH750 (product of Beckman Coulter, Inc., Miami, Fla.), which was equipped with non-focused apertures of a length of 100μ and a width of 80μ for measuring the prepared sample mixture as described above. The sample mixture was drawn through a set of three apertures (arranged in parallel) by a constant vacuum. The white blood cells were counted by a DC impedance measurement, and a histogram of the blood cells, after pulse editing, was also produced (averaged from the measurements of three apertures).

FIG. 1 shows a DC histogram of a normal whole blood sample analyzed on the experimental hematology analyzer as described above. As shown for a normal blood sample, the white blood cells had a bi-module distribution, with the lymphoid subpopulation on the left and the myeloid subpopulation on the right. No cell population located on the right side of the myeloid subpopulation. FIG. 2 shows a DC histogram of a clinical sample containing immature granulocytes analyzed according to the procedure described above. The manual reference reported about 12% of immature granulocytes (IG), including metamyelocytes, myelocytes and promyelocytes, which showed on the right side of the myeloid subpopulation. This sample had only 7% lymphocytes, and the majority of the white blood cells were myeloid population. FIG. 2A shows the DC histogram of another clinical sample containing about 6% of immature granulocytes including metamyelocytes and myelocytes, which were indicated by the large cells extending into the right-most region of the histogram. The manual reference also reported 5 NRBC per 100 WBC in this sample. As shown, NRBCs located on the left side of the lymphoid population, which was differentiated from the white blood cells.

FIGS. 3 and 4 show DC histograms of reference control compositions A and B analyzed using the same process as described above on the same instrument. As shown, the histogram of the reference control composition A resembles the cell distribution of the normal blood sample, and the histogram of the reference control composition B resembles the cell distribution of the clinical sample containing immature granulocytes.

FIGS. 5 and 6 show DC histograms of a normal whole blood sample and a clinical sample containing immature granulocytes analyzed on the same experimental hematology analyzer as described above, but with a larger dynamic range of the measurement. With the larger dynamic range, normal white blood cells distributed in approximately only half of the histogram. As shown, some of the immature granulocytes in this example were very large, and extended to the extreme right of the histogram.

FIG. 7 shows the DC histogram of reference control composition C analyzed on the experimental hematology analyzer with the same dynamic range shown in FIG. 5, which resembles the cell distribution of the clinical sample containing immature granulocytes.

EXAMPLE 5

Hematology Reference Control Composition Containing an Immature Granulocyte Component and Nucleated Red Blood Cell Component 1. NRBC Analog
   1. Select alligator whole blood having a red blood cell mean cell volume range from about 380 to about 460 fl. Centrifuge the alligator whole blood and remove the top layer (including white blood cells, platelets and plasma).
   2. Wash the packed alligator red blood cells three times with the phosphate buffered saline solution (PBS).
   3. Re-suspend the washed alligator red blood cells in one of the above-described suspension media. Preferably, the cell count is in a range from about $0.4 \times 10^6$ to about $0.6 \times 10^6$. The stabilized alligator red blood cells can be stored for a time period in excess of 45 days.

2. Prepare the Reference Control Composition

Procedure:
   1. Provide a predetermined volume of the Suspension Medium 1 described in Example 1.
   2. Add predetermined amounts of lymphoid and myeloid analogs of Example 3 in the suspension medium.
   3. Add a predetermined amount of immature granulocyte analog of Example 1 in the suspension medium.
   4. Add a predetermined amount of the NRBC analog in the suspension medium.

The cell concentrations of the white blood cell sub-components are prepared to simulate the corresponding cell concentrations of a human whole blood sample. The cell concentration of the immature granulocyte component is prepared to simulate a clinical sample containing a certain level of immature granulocytes, preferably in a range of 5% to 50% of total white blood cells. The cell concentration of the NRBC component is prepared to simulate a clinical sample containing a certain level of NRBCs, preferably in a range of 2 to 50 NRBC per 100 WBC.

This reference control composition can be used for the method of measuring immature granulocytes using a DC impedance measurement as described in Example 4, and can also be used for simultaneously measuring NRBC as described in co-pending patent application Ser. No. 10/770, 193, (now U.S. Pat. No. 6,916,658 issued on Jul. 17, 2005) which is herein incorporated by reference in its entirety.

EXAMPLE 6

Hematology Reference Control Composition Containing an Immature Granulocyte Component, Mature White Blood Cell Sub-Components, and Red Blood Cell and Platelet Components Procedure:

1. Provide a predetermined volume of the first suspension medium described in Example 1.

2. Add a predetermined amount of stabilized human red blood cells in the medium. The stabilized human red blood cells were processed following the procedure described in U.S. Pat. Nos. 4,299,726 and 4,358,394.

3. Add a predetermined amount of platelet analog in the suspension medium containing the stabilized human red blood cells. The platelet analog is made of fixed goat red blood cells following the procedure described in U.S. Pat. Nos. 4,264,470, 4,389,490 and 4,405,719.

4. Add predetermined amounts of lymphoid and myeloid analogs into the suspension medium containing the stabilized human red blood cells and platelet analog.

5. Add a predetermined amount of immature granulocyte analog into the suspension medium containing the stabilized human red blood cells, platelet analog and white blood cell component to form a reference control composition.

6. Mixing the reference control composition. The cell concentrations of the red blood cell, white blood cell and platelet components are prepared to simulate the corresponding cell concentrations of a human whole blood sample. The cell concentration of the immature granulocyte component is prepared to simulate a clinical sample containing a certain level of immature granulocytes, preferably in a range of 5% to 50% of total white blood cells.

While the present invention has been described in detail and pictorially shown in the accompanying drawings, these should not be construed as limitations on the scope of the present invention, but rather as an exemplification of preferred embodiments thereof. It will be apparent, however, that various modifications and changes can be made within the spirit and the scope of this invention as described in the above specification and defined in the appended claims and their legal equivalents. All patents and other publications cited herein are expressly incorporated by reference.

What is claimed is:

1. A method of using a hematology reference control to measure immature granulocyte comprising:
   (a) providing a reference control containing an immature granulocyte component made of processed red blood cells;
   (b) analyzing said reference control on a blood analyzer adapted for analyzing immature granulocytes, thereby said processed red blood cells in said reference control simulate immature granulocytes of a blood sample on said blood analyzer; and
   (c) reporting said immature granulocyte component of said reference control.

2. The method of claim 1, wherein said immature granulocyte component is made of avian, reptile, or fish red blood cells.

3. The method of claim 2, wherein said immature granulocyte component is made of alligator, emu, ostrich or shark red blood cells.

4. The hematology reference control of claim 3, wherein said immature granulocyte component is made of a mixture of said red blood cells of two different species, and said reference control simulates a broad size distribution of said immature granulocytes of said blood sample.

5. The method of claim 3, wherein said immature granulocyte component is in a size range from about 2% to about 85% larger than a high end of a size range of human granulocytes when measured by said blood analyzer.

6. The method of claim 3, wherein said reference control further comprises a mature white blood cell component simulating mature white blood cells in said blood sample, and said method further comprises reporting said mature white blood cell component of said reference control.

7. The method of claim 6, wherein a cell distribution of said immature granulocyte component and said mature white blood cell component of said reference control simulates a cell distribution of said blood sample on said blood analyzer.

8. The method of claim 1, wherein said analyzing said reference control is performed in a dynamic range from 0 to about 250 femtoliter (fL).

9. The method of claim 1, wherein said analyzing said reference control is performed in a dynamic range from 0 to about 400 femtoliter (fL).

10. The method of claim 1, wherein said analyzing said reference control is performed by an impedance measurement.

11. The method of claim 1, wherein said reference control is performed by an optical measurement.

12. The method of claim 11, wherein said optical measurement is a light scatter measurement.

13. The method of claim 11, wherein said optical measurement is axial light loss measurement.

* * * * *